United States Patent [19]

Krespan et al.

[11] 4,126,631
[45] Nov. 21, 1978

[54] β-CARBONYLPOLYFLUOROALKYL SULFONATE ESTERS

[75] Inventors: Carl G. Krespan; Bruce E. Smart, both of Wilmington, Del.

[73] Assignee: E. I. Du Pont de Nemours and Company, Wilmington, Del.

[21] Appl. No.: 775,596

[22] Filed: Mar. 8, 1977

Related U.S. Application Data

[63] Continuation-in-part of Ser. No. 602,757, Aug. 7, 1975, abandoned.

[51] Int. Cl.² .................... C07C 143/68; C08F 4/00
[52] U.S. Cl. ........................ 260/456 F; 260/458 F; 260/513 F; 568/685; 528/408
[58] Field of Search ............................ 260/456 F

[56] References Cited

PUBLICATIONS

England et al., JACS, 82, 6181 (1960).
Sokol'Skii et al., IZV. Akad. Nauk SSSR, Ser. Khim., 7, 1524 (1967), (English Translation).
Belaventsey et al., Ibid, 10, 2296 (1968), (English Translation).

Primary Examiner—Nicky Chan

[57] ABSTRACT

Novel β-carbonylpolyfluoroalkyl sulfonate esters, e.g.,

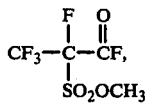

are prepared by reacting $SO_3$ with the corresponding acyclic fluorovinyl esters, e.g., $CF_3CF{=}CFOCH_3$, at a temperature of about $-40°$ to $110°$ C. These esters are useful as very active cationic initiators, e.g., for the polymerization of tetrahydrofuran.

5 Claims, No Drawings

β-CARBONYLPOLYFLUOROALKYL SULFONATE ESTERS

RELATED APPLICATION

2-Ketopentafluoropropanesulfonic acid, disclosed herein, is claimed in coassigned application Ser. No. 602,756, filed Aug. 7, 1975. This application is a continuation-in-part of Ser. No. 602,757, filed Aug. 7, 1975, now abandoned.

BACKGROUND OF THE INVENTION

1. Field of the Invention

This invention relates to certain sulfonate esters and processes for producing them.

2. Prior Art

A. F. Eleev et al., Izv. Akad. Nauk, SSSR Ser. Khim 397 (1974); Chem Abstr., 81 24973t (1974), disclose the reactions:

a. $(CF_3)_2C=CF_2 + HOCH_2CH_2Cl \rightarrow$
$(CF_3)_2C=C(OCH_2Cl)_2$
b. $(CF_3)_2C=C(OCH_2CH_2Cl)_2 + SO_3$
$\rightarrow [ClCH_2CH_2OSO_2C(CF_3)_2CO_2CH_2CH_2Cl]$ "Presumed Intermediate"

c. $[ClCH_2CH_2OSO_2C(CF_3)_2CO_2CH_2CH_2Cl] \xrightarrow{120° C.}$
$CF_3)_2CHSO_2OCH_2CH_2Cl$ I. L. Knunyants and G. A. Sokol'skii, Angew. Chem, Internat. edit., 11 583 (1972) review the synthesis and chemistry of fluorinated β-sulfones and include mention of β-sulfones from $FClC=CFOCH_3$ and $FClC=CFOC_2H_5$, along with 2:1 $SO_3$/olfein cycloadducts from $(CF_3)_2C=CFOCH_3$ and $(CF_3)_2C=CFOC_2H_5$.

G. A. Sokol'skii et al., Izv. Akad. Nauk SSSR, Ser. Khim., No. 7, 1524–1527 (1967) describe the mechanism by which diesters are formed from fluorinated β-sultones. M. A. Belaventsev et al., Izv. Akad. Nauk SSSR, Ser. Khim., No. 10, 2296-2303 (1968) describe the reaction of $SO_3$ with $CFCl=CF-O-R$ to obtain the sultone $$\begin{array}{c} CFCl \\ SO_2 \diagup \diagdown CF-OR. \\ \diagdown O \diagup \end{array}$$

The correct product of this reaction is

FCCl—COF
|
$SO_2OR$.

Neither of these references disclose a utility for the described compounds.

SUMMARY OF THE INVENTION

The present invention provides β-carbonylpolyfluoroalkyl sulfonate esters of the formula $$R^1-\overset{O}{\underset{\|}{C}}-CFR^3SO_2OR^4$$

wherein $R^1$ and $R^3$ and F or perfluoroalkyl of up to 8 carbon atoms provided that $R^1$ and $R^3$ are not both F; and $R^4$ is $CH_3$ or $CH_2CH_3$.

The invention also provides a process wherein said esters are prepared by reacting acyclic fluorovinyl esters of the formula $$R^1-\overset{OR^4}{\underset{|}{C}}=CFR^3,$$

wherein $R^1$, $R^3$ amd $R^4$ are as defined above, with sulfur trioxide.

$$R^1-\overset{OR^4}{\underset{|}{C}}=CFR^3 + SO_3 \rightarrow R^1-\overset{O}{\underset{\|}{C}}-\overset{F}{\underset{|}{\underset{R^3}{C}}}-SO_2OR^4.$$

The preparation of the fluorinated ethers used as precursors in this reaction is shown, for example, by England, et al., J. Fluorine Chem., 3 63 (1973/74) and Wiley, et al., J. Org. Chem., 29, 1876 (1964).

The reaction is preferably carried out in liquid phase, at a temperature varying from about −40° to + 100° C., and preferably at about 0°–50°. The reaction time can be short, the reaction in many cases being completed within a few minutes at higher temperatures, e.g., 50°–100° C. but can be as long as a day, e.g., at −40 to +40° C. Atmospheric pressure is generally preferred, but pressures up to 3000 psi (0.2 kilobars) can be employed.

A solvent is not necessary, but solvent media having little or no reactivity toward $SO_3$ may be used, especially halogenated solvents such as tetrachloroethylene and 1,1,2-trichloro-1,2,2-trifluoroethane. An excess of either reactant can be used if desired, but a mole ratio of the acyclic fluorovinyl ether to $SO_3$ close to 1:1 is preferred. Isolation is generally effected by distillation under reduced pressure.

The novel monomers of this invention are colorless oils of moderate to high boiling points. They are useful as active cationic initiators, e.g., for the polymerization of tetrahydrofuran, desirable as a soft segment in polyurethanes. These soft segments lend very desirable properties to polyurethanes used as spandex fibers.

DESCRIPTION OF THE PREFERRED EMBODIMENTS

The following examples illustrate the present invention. In these examples, temperature is in degrees centigrade. Percentages are given by weight.

EXAMPLE 1

Ethyl 2-ketopentafluoropropane sulfonate (III)

$$\underset{I}{CF_3\overset{OCH_2CH_3}{\underset{|}{C}}=CF_2} + SO_3 \rightarrow$$

$$\underset{III}{CF_3\overset{O}{\underset{\|}{C}}CF_2SO_2OCH_2CH_3} + \underset{II}{CF_3\overset{O}{\underset{\|}{C}}CF_2SO_2OH}$$

A. Dropwise addition of 12.8 g (0.16 mol) of $SO_3$ to 29.0 g (0.165 mol) of ethyl pentafluoroisopropenyl ether (I; D. W. Wiley and H. E. Simmons, J. Org. Chem., 29, 1876 (1974)) resulted in an exothermic reaction. Distillation of the black reaction mixture gave 6.3 g (22%) of crude recovered propenyl ether (identified by ir) and 20.2 g (49% conversion and 63% yield) of III bp 47°–48° (12 mm).

Spectral properties fit ring-opened ester III as the structure of the title compound. Ir (neat) 3.34 and 3.41 (satd CH), 5.60 (C=O), 7.09 (SO$_2$O), 7.6–8.5 $\mu$ (CF,SO$_2$): nmr $^1H$ 4.59 (q, $J_{HH}$ 7.2 Hz, 2,OCH$_2$), 1.51 ppm (t, $J_{HH}$7.2 Hz, 3, CH$_3$); $^{19}$F-75.0 (t,$J_{FF}$8.3 Hz, 3,CF$_3$), −107.4 ppm (q, $J_{FF}$8.3 Hz,2,CF$_2$).

B. Reaction of 176 g (1.0 mol) of ethyl pentafluoroisopropenyl ether and 88 g (1.1 mol) of SO$_3$ was carried out similarly to A above, but at 0°–5°. The colorless reaction mixture, which darkened on standing overnight, was distilled to give 28.6 g (16% of crude recovered vinyl ether, bp 46°–48°; 145.1 g (57% conv and 68% yield) of III, bp 48°–52° (12 mm); and a higher boiling cut composed mainly of 2-ketopentafluoropropanesulfonic acid (II). Redistillation of the crude II gave 35.6 g (16% conv and 19% yield) of II, bp 81°–82°(6.2 mm).

The use of compound III is illustrated below in Utility Example A.

EXAMPLE 2

Methyl 1-Fluorocarbonyltetrafluoroethanesulfonate (X)

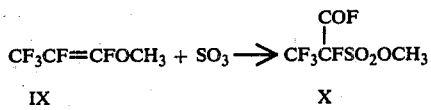

$$CF_3CF=CFOCH_3 + SO_3 \longrightarrow CF_3\overset{COF}{\underset{|}{C}}FSO_2OCH_3$$

IX                                     X

To 48.6 g (0.30 mol) of impure 1-methoxy pentafluoropropene IX; 86% trans/14% cis) stirred at −20° to −10° was added dropwise 28.0 g(0.35 mol) of SO$_3$ (vigorous reaction). After addition has been completed, the mixture was stirred overnight at 25° and distilled to give 26.6 g (37%) of the title sulfonate X, bp 64° (60 mm) along with considerable tarry residue. Ir (neat) 3.33 and 3.47 (satd CH), 5.34 (COF), 7.07 (SO$_2$O), 7.7 – 9 $\mu$ (CF,SO$_2$): nmr $^1$F 4.26 ppm (s,OCH$_3$); $^{19}$F 32.0 (d,$J_{FF}$ 23.2 Hz into overlapping q, $J_{FF}$ 7.6 Hz, COF), −73.5 (D,$J_{FF}$7.6 Hz, into overlapping d, $J_{FF}$7.6 Hz, 3, CF$_3$), −162.8 ppm (d, $J_{FF}$23.2 Hz, into overlapping q, $J_{FF}$ 7.6 Hz, 1,CF).

Anal. Calcd for C$_4$H$_3$F$_5$O$_4$S: C, 19.84; H, 1.25; F, 39,24;
S, 13.24.
Found: C, 20.07; H, 1.33; F, 39.06;
S, 13.07.

The use of compound X is illustrated below in Utility Example B.

The preparation of cis- and trans-CF$_3$CF=CFOCH$_3$ is given in D. C. England, L. Solomon, and C. G. Krespan, J. Fluorine Chem., 3, 63 (1973/74).

EXAMPLE 3

Methyl 2-Keto-1-Trifluoromethyltetrafluoropropanesulfonate (XIII)

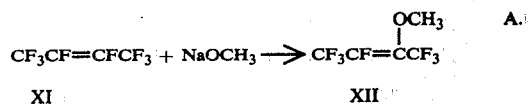

A.
$$CF_3CF=CFCF_3 + NaOCH_3 \longrightarrow CF_3CF=\overset{OCH_3}{\underset{|}{C}}CF_3$$

XI                                     XII

A suspension of 27.0 g (0.50 mol) of sodium methoxide in 300 ml of dry diglyme was stirred at −40° while 100 g (0.50 mol) of perfluorobutene-2 (XI) was distilled in. The mixture was then stirred at −40° for 15 min, at 5° for 45 min, and at 25° for 4 hr. Distillation afforded 70.9 g (67%) of 2-methoxyheptafluorobutene-2 (XII), bp 50°–58°. A sample of XII prepared similarly in tetrahydrofuran and washed with water to remove solvent has bp 50°–52° and was analyzed. Ir (CCl$_4$) 3.37 and 3.48 (satd CH), 5.92 (C=C), 7.5-9 $\mu$ (CF, COC): nmr $^1$H 3.82 ppm (m,OCH$_3$); $^{19}$F-66.5 (d,$J_{FF}$1.5 Hz,3,CF$_3$), −148.1 ppm (q,$J_{FF}$ 22.3 Hz, into overlapping q, $J_{FF}$ 8.1 Hz, 1,CF) for trans isomer with minor amounts of cis isomer present.

Anal. Calcd for C$_5$H$_3$F$_7$O: C, 28.32; H, 1.43; F, 62.71.
Found: C, 28.05; H, 1.32; F, 62.62.

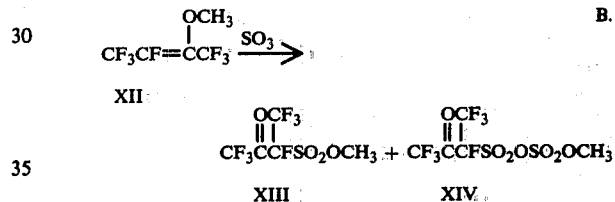

B.
$$CF_3CF=\overset{OCH_3}{\underset{|}{C}}CF_3 \xrightarrow{SO_3}$$

XII $$CF_3\overset{OCF_3}{\underset{||}{C}}CFSO_2OCH_3 + CF_3\overset{OCF_3}{\underset{||}{C}}CFSO_2OSO_2OCH_3$$

XIII                                    XIV

To 36.0 g (0.17 mol) of XII stirred at 30° was added dropwise 16.0 g (0.20 mol) of SO$_3$ from a freshly opened ampoule. The mixture was stirred 30 min and distilled to give a small amount of CF$_3$CHFCOCF$_3$, then a mixture of SO$_3$ and starting olefins bp 50°–68°, with only 3.6 g of product, bp 52-57° (25 mm). The lower distillation cuts were recombined, another 16.0 g (0.20 mol) of SO$_3$ was added, and the mixture refluxed 2 hr. The pot temperature rose from 50° to 68° and leveled during this period. Distillation afforded 9.3 g of the title sulfonate XIII, bp 60°–61° (25 mm), for a total of 12.8 g (26%) with previous distillate, and 21.0 g (33%) of XIV, the mixed anhydride of 2-keto-1-trifluoromethyltetrafluoropropanesulfuric acid with methyl sulfate, bp 89°–90° (10 mm). For XIII, ir (neat) 3.36 (satd CH), 5.62 (C=O),7.08 (SO$_2$O), 7.5–9 $\mu$(CF,SO$_2$): nmr $^1$H 4.25 ppm (s,OCH$_3$); F-73.3 (d,$J_{FF}$ 7.6 Hz, into q, $J_{FF}$ 1.5 Hz,3, CF$_3$), −75.5 (d, $J_{FF}$ 18.5 Hz, into q, $J_{FF}$ 1.5 Hz, 3, CF$_3$), -173.7 ppm (q, $J_{FF}$ 18.5 Hz, into overlapping q, $J_{FF}$ 7.6 Hz, 3,CF$_3$).

Anal. Calcd for C$_5$H$_3$F$_7$O$_4$S: C, 20.56; H, 1.04; F, 45.52; S, 10.97. Found: C, 20.42; H, 1.18; F, 45.79; S, 10.98.

For XIV:ir (CaF$_2$ plates) 3.37 (satd CH), 5.60 (C=O), 6.98 (SO$_2$O), 7.9–5 $\mu$ (CF,SO$_2$): nmr $^1$H 4.30 ppm (s,OCH$_3$); $^{19}$F-72.4 (d,$J_{FF}$7.9 Hz, into q, $J_{FF}$ 1.5 Hz,3, −75.2 (d,$J_{FF}$ 18.3 Hz, into q, $J_{FF}$ 1.5 Hz, 3, CF$_3$), −170.3 ppm (q, $J_{FF}$ 18.3 Hz, into overlapping q, $J_{FF}$ 7.9 Hz,1, CF).

Anal. Calcd for C$_5$H$_3$F$_7$O$_7$S$_2$: C, 16.14; H, 0.81; F, 35.73; S, 17.23. Found: C, 16.26; H, 0.96; F, 36.34; S, 17.20.

EXAMPLE 4

Methyl 1-Fluorocarbonylperfluorohexane-1-sulfonate (XVIII)

A.

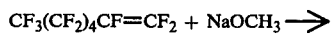

XV

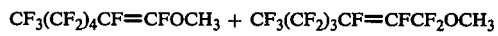

XVI          XVII

A suspension of 7.60 g (0.14 mol) of sodium methoxide in 100 ml of dry glyme was stirred at $-50°$ while 49.4 g (0.14 mol) of perfluoro-n-heptene-1(XV) was added rapidly during 5 min. The resulting mixture was stirred at $-40°$ to $-30°$ for 30 min, $-20$ to $-10°$ for 30 min, and then overnight at 25°. The reaction mixture was diluted with 500 ml of water, and the lower product layer was washed with 100 ml of water, dried and distilled. Fractions collected bp 45°–54° (50 mm) were shown to be mainly trans isomer of methyl perfluoroheptene-2-yl ether (XVII), 10.6 g (21%). Fractions bp mainly 66°–68° (50 mm), 16.5 g (33%), were a mixture of cis and trans-methyl perfluoro-n-heptene-1-yl ether (XVI). Ir: 3.30, 3.35, and 3.47 (satd CH), 5.69 (CF=CFO—), 7.5–9 $\mu$ (CF,COC). Nmr (CCl$_4$) $^1$H 3.98 (m,7, trans CR=CFOCH) and 3.88 ppm (m,3, cis CF=CFOCH$_3$) with impurity peak at 3.70; $^{19}$F-81.7 (t, J$_{FF}$=10 Hz, into t, J$_{FF}$=2 Hz,3,CF$_3$), $-92.1$ (d,J$_{FF}$=18 Hz, into t, J$_{FF}$=7 Hz, 0.3, cis CF=CFOCH$_3$, $-111.4$ (d,J$_{FF}$=119 Hz, into t, J$_{FF}$=28 Hz, into m, 0.7, trans CF=CFOCH$_3$), $-117.5$ (m,2,CF$_2$), $-123.8$ (broad,2,CF$_2$), $-127.1$ (m,2,CF$_2$)$-183.5$, (broad, 0.3, cis- CF=CFOCH$_3$), and $-191.7$ ppm (d,J$_{FF}$=119 Hz, 0.7, trans-CF=CFOCH$_3$).

Anal. Calcd for C$_8$H$_3$F$_{13}$O: C, 26.54; H, 0.83; F, 68.21 Found: C, 26.71; H, 0.78; F, 68.13

B.

XVI

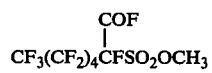

XVIII

Sulfur trioxide (3.3 g, 0.041 mol) was added dropwise to 14.7 g (0.041 mol) of cis- and trans-perfluoro-n-heptene-1-yl ether cooled at 0.5°. The reaction mixture was allowed to come to 25°, stirred there for one hr, and then distilled to give 4.6 g (31%) of recovered olefin XVI and 2.6 g (15% conv, 22% yield) of the title sulfonate ester XVIII, bp 55–58 (2.4 mm). Ir (CCl$_4$): 3.36 (satd CH), 5.37 (COF), 7.04 (SO$_2$O), and 7.5–9 $\mu$ (CF,SO$_2$). Nmr (CCl$_4$): $^1$H 4.27 ppm (s,OCH$_3$); $^{19}$F 31.6 (d,J$_{FF}$=24 Hz, into overlapping triplets, J$_{FF}$=12 Hz,1,COF), $-81.6$ (t, J$_{FF}$=10.2 Hz, into t,J$_{FF}$=2.2 Hz,3,CF$_3$), $-116.1$ (broad,2,CF$_2$), and $-161.3$ ppm (d,J$_{FF}$=25 Hz, into overlapping T,J$_{FF}$~12 Hz, into t,J$_{FF}$~12 Hz,1,CF).

Anal. Calcd for C$_8$H$_3$F$_{13}$O$_4$S: C, 21.73; H, 0.68. Found: C, 21.67; H, 0.73.

UTILITY EXAMPLES A AND B

The monomers of this invention are very active cationic initiators. Results on THF (tetrahydrofuran) polymerization with two of the monomers are given in the following Table. Polymerizations were run in bulk at about 25°, ten grams of purified THF being used in each run. In both cases, viscosity increased markedly in 30 min, but the polymerizations were allowed to proceed for one day. Work-up was by quenching with 50 ml of concentrated NH$_4$OH plus 50 ml of distilled water, thorough washing with 10 ml of concentrated NH$_4$OH plus 90 ml of distilled water, followed by drying at 50° under full pump vacuum.

TABLE

| Example Number | Initiator | Weight of Initiator (g) | Weight of Polymer Yield (g) | (0.1% in (CF$_3$)$_2$CHOH at 25° C) |
|---|---|---|---|---|
| A | Compound III of Example 1 | 0.07 | 7.82 | 2.30 |
| B | Compound X of Example 2 | 0.06 | 7.70 | 2.05 |

Polytetrahydrofuran is a hydrolytically stable soft segment with good low temperature properties for incorporation into polyurethanes useful as elastomers and as spandex fibers. F. Rodriquez, "Principles of Polymer Systems," McGraw-Hill, New York, N. Y., 1970, p. 424, for example, cites homopolymers of tetrahydrofuran in the mol. wt. range 1000–3000, obtainable here by the addition of small amounts of water during polymerization, as useful components with diisocyanates for preparing polyurethanes.

We claim:

1. A $\beta$-carbonylpolyfluoroalkyl sulfonate ester of the formula $$R^1-\overset{O}{\underset{\|}{C}}-CFR^3-SO_2OR^4,$$

wherein:
   $R^1$ and $R^3$ are fluorine or perfluoroalkyl of up to 8 carbons provided that $R^1$ and $R^3$ are not both fluorine; and
   $R^4$ is methyl or ethyl.

2. The compound of claim 1, ethyl 2-ketopentafluoropropanesulfonate.

3. The compound of claim 1, methyl 1-fluorocarbonyltetrafluoroethanesulfonate.

4. The compound of claim 1, methyl 2-keto-1-trifluoromethyltetrafluoropropanesulfonate.

5. The compound of claim 1, methyl 1-fluorocarbonylperfluorohexane-1-sulfonate.

* * * * *